(12) United States Patent
Cary

(10) Patent No.: US 8,802,910 B2
(45) Date of Patent: Aug. 12, 2014

(54) ALKYLATION OF AROMATIC SUBSTRATES AND TRANSALKYLATION PROCESS

(75) Inventor: Jean-Bernard Cary, Le Havre (FR)

(73) Assignee: Total Petrochemicals France, Paris (FR)

( * ) Notice: Subject to any disclaimer, the term of this patent is extended or adjusted under 35 U.S.C. 154(b) by 417 days.

(21) Appl. No.: 12/937,581

(22) PCT Filed: Apr. 3, 2009

(86) PCT No.: PCT/EP2009/053992
§ 371 (c)(1),
(2), (4) Date: Jan. 26, 2011

(87) PCT Pub. No.: WO2009/127533
PCT Pub. Date: Oct. 22, 2009

(65) Prior Publication Data
US 2011/0130608 A1    Jun. 2, 2011

(30) Foreign Application Priority Data

Apr. 18, 2008  (EP) .................................... 08290392

(51) Int. Cl.
*C07C 2/66*  (2006.01)

(52) U.S. Cl.
USPC ......................................... 585/448; 565/467

(58) Field of Classification Search
CPC ................................ C07C 2/66; C07C 15/073
USPC ................................................. 585/448, 467
See application file for complete search history.

(56) References Cited

U.S. PATENT DOCUMENTS

| 7,199,275 B2 | 4/2007 | Smith |
| 2007/0179329 A1 | 8/2007 | Clark |

FOREIGN PATENT DOCUMENTS

| JP | 2000-131225 A | 5/2000 |
| JP | 2004-069346 A | 3/2004 |
| WO | 00/35836 A1 | 6/2000 |
| WO | 2006/032400 A1 | 3/2006 |

OTHER PUBLICATIONS

Surinder (Sandy) Thind: "The on-line detection of oxides of nitrogen in light hydrocabon strams by modified chemiluminescence detection and/or by dry colorimetric detection". May 2005. XP002499608. URL:http://www.ciarialytics.com.
Surinder (Sandy) Thind: "Analysis of impurities in Polymer-grade ethyiene, propylene and 1,3-butadiene" Jul. 2003, XP002499609, URL:http//cianalytics.com.
Anonymous "Ultra-sensitice analyzers for online and laboratory applications", URL:http//www.cianalytics.com.
Japanese Office Action issued in Japanese Application No. 2011-504412 mailed on Apr. 30, 2013 and English translation thereof (5 pages).
Office Action and Search Report issued in Chinese Application No. 200980123312.9 mailed on Jan. 27, 2014, and English translation thereof, 23 pages.

*Primary Examiner* — Thuan D Dang

(57) ABSTRACT

A process for the alkylation of an aromatic substrate can include providing an alkylation reaction zone containing an alkylation catalyst, and introducing a feedstock including an aromatic substrate and an alkylating agent into an inlet of the alkylation reaction zone and into contact with the alkylation catalyst. The alkylation reaction zone can be operated at temperature and pressure conditions to cause alkylation of the aromatic substrate in the presence of the alkylation catalyst to produce an alkylation product including a mixture of the aromatic substrate and monoalkylated and polyalkylated aromatic components. The alkylation product can be withdrawn from the alkylation reaction zone. Nitrogen containing compounds in the aromatic substrate, alkylating agent, or both can be monitored in a range 15 wppb to 35 wppm by dry colorimetry. The process can include transalkylation of polyalkylated aromatic components in a transalkylation reaction zone containing a transalkylation catalyst.

5 Claims, No Drawings

ALKYLATION OF AROMATIC SUBSTRATES AND TRANSALKYLATION PROCESS

FIELD OF THE INVENTION

The present invention relates to the alkylation of aromatic substrates and related transalkylation process. The alkylation of aromatic substrates such as benzene to produce alkylated aromatics such as ethylbenzene and diethylbenzene are known in the art. More precisely the invention relates to the monitoring of the nitrogen containing compounds impurities in the aromatic substrate feedstock and/or in the alkylating agent feedstock. The transalkylation of polyalkylated aromatics such as diethylbenzene with an aromatic substrate such as benzene to produce alkylated aromatics such as ethylbenzene is known in the art. The present invention also relates to the monitoring of the nitrogen containing compounds impurities in the aromatic substrate feedstock of said transalkylation process.

BACKGROUND OF THE INVENTION

Alkylation and transalkylation processes using catalysts are often subject to catalyst regeneration and replacement requirements resulting from poisoning of the catalyst by one or more impurities contained in the hydrocarbon feedstock. In many cases, catalyst developments, e.g. to reduce coke-forming and other by-product reactions, have progressed to the stage where poisoning by feedstock impurities is the primary reason that catalyst performance deteriorates which forces the catalyst to be replaced or regenerated. Aromatics alkylation processes employing molecular sieve catalysts can be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve catalysts tend to be more sensitive to the presence of impurities in the feedstocks, particularly polar compounds such as nitrogen compounds. Such impurities reduce the acid activity of the catalyst and hence decrease the cycle time between required regenerations of the catalyst. Various processes have been developed for removal of such impurities prior to contact with the catalyst. In the following prior arts there are description of said impurities as well as processes to remove these impurities.

U.S. Pat. No. 6,002,057 describes a process for the alkylation of an aromatic hydrocarbon contained in a hydrocarbon stream comprising:
(a) separating essentially all aromatics other than said aromatic hydrocarbon from said hydrocarbon stream, thereby forming an aromatic-rich stream;
(b) treating said aromatic-rich stream of (a) by converting essentially all olefinic compounds contained therein by hydrogenation;
(c) contacting the thus treated aromatic-rich stream from (b) with an olefin-containing stream comprising at least one olefin selected from the group consisting of ethylene, propylene, and butylene, wherein the molar ratio of the olefin(s) to said aromatic hydrocarbon is not less than 1 in the presence of a catalyst comprising zeolite beta, under alkylation conditions, whereby mono and polyalkylated aromatics are formed; and
(d) separating said mono and polyalkylated aromatics formed in (c) from the remaining hydrocarbons.

At col 6 lines 48-53 is mentioned that the olefins may be present in admixture with hydrogen, methane, C2 to C4 paraffins, but it is usually preferable to remove dienes, acetylenes, sulfur compounds or basic nitrogen compounds (NH3 or amines) which may be present in the olefin feedstock stream, to prevent rapid catalyst deactivation.

U.S. Pat. No. 6,617,482 describes a process for removing polar compounds from an aromatic feedstock which contains polar compounds and which is then used in an alkylation process. The process comprises contacting the feedstock in an adsorption zone at a temperature of less than or equal to 130° C. with an adsorbent selective for the adsorption of said polar compounds and comprising a molecular sieve having pores and/or surface cavities with cross-sectional dimensions greater than 5.6 Angstroms. A treated feedstock substantially free of said polar compounds is withdrawn from the adsorption zone and fed to an alkylation zone for contact under liquid phase alkylation conditions with an alkylating agent in the presence of an alkylation catalyst. More particularly, this prior art relates to a liquid phase aromatics alkylation process which includes subjecting the aromatic feedstock to a pretreatment step for the selective removal of polar contaminants that poison aromatic alkylation catalysts. Such contaminants include nitrogen, sulfur, and oxygen containing compounds, particularly those that boil in the same ranges as benzene, toluene or xylenes.

US 2005 0143612 describes a process for the production of alkyl aromatic compounds wherein aromatic compounds which may be treated for removal of deleterious substances are reacted with olefin compounds, which may also be treated for contaminant removal, in the presence of acidic zeolite catalyst(s) to produce the desired alkyl aromatic compound (s). The aromatic and preferably also the olefin feeds are treated substantially to remove contaminants, particularly the nitrogen compounds contained therein, before they are brought together for reaction in the presence of the zeolite catalyst(s). The feed pretreatment for removal of nitrogen compounds significantly improves the run length and life of the acidic zeolite catalyst(s). A specific object of this prior art is to provide methods and apparatus for treating an olefin or aromatic feedstock for removal of organic or inorganic nitrogen compounds in preparation for a catalytic alkylation or transalkylation process. In accordance with said prior art, it has been found that nitrogen-containing impurities in one or both feedstocks may neutralize the acidic active sites on the acidic zeolite catalyst and thereby reduce catalyst activity and its ability to effect the desired reaction. Long-term accumulation of these nitrogen-containing impurities on the catalyst gradually reduces catalyst activity to the point where plant performance becomes unacceptable, requiring that the plant be shutdown to reactivate, regenerate, or replace the catalyst.

U.S. Pat. No. 7,199,275 relates to a process for alkylation of an aromatic hydrocarbon stream comprising impurities in which said impurities are removed in a pretreatment system having a first stage, a second stage located downstream of said first stage and a cycle length, said process comprising the steps of:
(a) contacting the aromatic hydrocarbon stream with a first molecular sieve which is 13X in said first stage of said pretreatment system, to remove at least a portion of said impurities, to produce a partially treated aromatic hydrocarbon stream;
(b) contacting said partially treated aromatic hydrocarbon stream with a second molecular sieve which is 4A in a second stage of said pretreatment system to remove substantially all of the remaining portion of said impurities, and to produce a fully treated aromatic hydrocarbon stream; and
(c) contacting said fully treated aromatic hydrocarbon stream with an alkylating agent in the presence of an alkylation catalyst and under alkylation conditions, to produce an alkylated aromatic hydrocarbon stream; and wherein said cycle length of said pretreatment system is greater than said cycle length using said first stage of said pretreatment system alone or said second stage of said pretreatment system alone.

In a preferred embodiment the process further comprises the step of contacting said alkylating agent of step (c) with a third molecular sieve, to produce a treated alkylating agent, and contacting said treated alkylating agent with said treated aromatic hydrocarbon stream of step (b), to produce said alkylated aromatic hydrocarbon stream of step (c).

However the above prior arts are silent on how to check these impurities in an industrial process. It has now been discovered that by dry colorimetry it was possible to get in less than 5 minutes the amount of the nitrogen containing compounds impurities in the aromatic substrate or in the alkylating agent. A sample of the feedstock to be analyzed is vaporized, unless it is available under gasous phase, and is sent through a porous substrate carrying a reagent which changes color in proportion with the impurities. An electronic device converts the color to the amount of impurities. To improve the response in time, many such apparatus can be used in parallel and a measurement is launched e.g. every minute or every ten seconds. Should the impurities are found to be higher than a requested level the reactor containing the catalyst can be temporarily by-passed.

BRIEF SUMMARY OF THE INVENTION

The present invention is a process for the alkylation of an aromatic substrate comprising:
(a) providing an alkylation reaction zone containing an alkylation catalyst;
(b) introducing a feedstock comprising an aromatic substrate and an alkylating agent into the inlet of said alkylation reaction zone and into contact with said alkylation catalyst;
(c) operating said alkylation reaction zone at temperature and pressure conditions to cause alkylation of said aromatic substrate in the presence of said alkylation catalyst to produce an alkylation product comprising a mixture of said aromatic substrate and monoalkylated and polyalkylated aromatic components;
(d) withdrawing the alkylation product from said alkylation reaction zone;
wherein
the nitrogen containing compounds impurities in the aromatic substrate or in the alkylating agent or both in the aromatic substrate and in the alkylating agent are monitored in a range 15 wppb-35 wppm by dry colorimetry.

In an advantageous embodiment the alkylation reaction zone is operated in the liquid phase.

In another embodiment the aromatic substrate is benzene and the alkylating agent is ethylene.

The present invention also relates to a process for the transalkylation of polyalkylated aromatic components comprising:
(a) providing a transalkylation reaction zone containing a transalkylation catalyst;
(b) introducing a feedstock comprising at least a polyalkylated aromatic component deriving from an aromatic substrate into the inlet of said transalkylation reaction zone and into contact with said transalkylation catalyst;
(c) supplying an aromatic substrate to said transalkylation zone, said aromatic substrate being the same as the one of step (b);
(d) operating said transalkylation zone at temperature and pressure conditions to cause disproportionation of said polyalkylated aromatic components to produce a disproportionation product having a reduced polyalkylated aromatic content and an enhanced monoalkylated aromatic content;
(e) withdrawing the disproportionation product from said transalkylation zone;
wherein
the nitrogen containing compounds impurities in the aromatic substrate are monitored in a range 15 wppb-35 wppm by dry colorimetry.

In an advantageous embodiment the aromatic substrate is benzene and the polyalkylated aromatic component is diethylbenzene.

DETAILED DESCRIPTION OF THE INVENTION

As regards the catalysts that can be used for alkylation of benzene with propylene and also for transalkylation of benzene and polyisopropylbenzenes in liquid phase include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia, all of which are known in the art.

Catalysts that can be used for alkylation of benzene with ethylene and transalkylation of benzene and polyethylbenzenes in liquid phase processes include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia.

Most of these catalysts are described in the following patents: WO 2007/081923, EP 0485683, EP 0467007, EP 0507761, EP 1 691 923, EP 0 826 653, EP 0 733 608, EP 0 726 242, EP 0 844 023, EP 0 879 809, EP 943594, EP 1043296, EP 1059277, EP 1002778, EP 1031549, U.S. Pat. No. 6,268, 305, EP 1188734, EP 1211233, EP 1208907, EP 1556318, EP 1546071, EP 1727860, EP 1581466, EP 1807201, EP1851184, the content of each is incorporated by reference in the present application.

MCM-22 and its use to catalyze the synthesis of alkyl aromatics are described, for example, in U.S. Pat. No. 4,954, 325 (Rubin), U.S. Pat. No. 4,992,606 (Kushnerick), U.S. Pat. No. 5,077,445 (Le), U.S. Pat. No. 5,334,795 (Chu), and U.S. Pat. No. 5,900,520 (Mazzone), each of which is incorporated herein by reference. MCM-36 and its use in the synthesis of alkyl aromatics are described in U.S. Pat. No. 5,250,277 (Kresge), U.S. Pat. No. 5,292,698 (Chu), and U.S. Pat. No. 5,258,565 (Kresge), each of which is incorporated herein by reference. MCM-49 and its use in the synthesis of alkyl aromatics are described in U.S. Pat. No. 5,236,575 (Bennett), U.S. Pat. No. 5,493,065 (Cheng) and U.S. Pat. No. 5,371,310 (Bennett), each of which is incorporated herein by reference. MCM-56 and its use to catalyze the synthesis of alkyl aromatics are described in U.S. Pat. No. 5,362,697 (Fung), U.S. Pat. No. 5,453,554 (Cheng), U.S. Pat. No. 5,536,894 (Degnan), U.S. Pat. No. 5,557,024 (Cheng), and U.S. Pat. No. 6,051,521 (Cheng), each of which is incorporated herein by reference. MCM-58 and its use for the production of alkyl aromatics are described in U.S. Pat. No. 5,437,855 (Valyocsik) and U.S. Pat. No. 5,569,805 (Beck), each of which is incorporated herein by reference. MCM-68 and its use for the production of alkyl aromatics are described in U.S. Pat. No. 6,049,018 (Calabro), which is incorporated herein by reference.

The use of tungstate modified zirconia to catalyze the synthesis of alkyl aromatics is described in U.S. Pat. No. 5,563, 311 (Chang), which is incorporated herein by reference. U.S.

Pat. No. 5,081,323 (Innes), which is incorporated herein by reference, teaches a liquid phase alkylation or transalkylation process using zeolite beta. Production of cumene over zeolite Y is described in U.S. Pat. No. 5,160,497 (Juguin) and U.S. Pat. No. 5,240,889 (West), which are incorporated herein by reference. U.S. Pat. No. 5,030,786 (Shamshoum) and U.S. Pat. No. 5,980,859 (Gajda), and European patent 0,467,007 (Butler), which are incorporated herein by reference, describe the production of alkyl aromatic compounds with zeolite Beta, zeolite Y, and zeolite Omega U.S. Pat. No. 5,522,984 (Gajda), U.S. Pat. No. 5,672,799 (Perego), U.S. Pat. No. 5,980,859 (Gajda), and U.S. Pat. No. 6,162,416 (Gajda), which are incorporated herein by reference, teach the production of cumene with zeolite beta. Use of zeolite Mordenite in production of monoalkylated benzene such as cumene and ethylbenzene is described in U.S. Pat. No. 5,198,595 (Lee), which is incorporated herein by reference. Production of ethylbenzene with ex situ selectivated zeolite catalyst is described in U.S. Pat. No. 5,689,025 (Abichandani), which is incorporated herein by reference. Production of ethylbenzene with ZSM-5 is described in U.S. Pat. No. 5,157,185 (Chu), which is incorporated herein by reference.

Production of ethylbenzene over intermediate pore size zeolites is described in U.S. Pat. No. 3,751,504 (Keown), U.S. Pat. No. 4,547,605 (Kresge), and U.S. Pat. No. 4,016,218 (Haag), which are incorporated herein by reference. U.S. Pat. No. 4,169,111 (Wight) and U.S. Pat. No. 4,459,426 (Inwood), which are incorporated herein by reference, disclose production of ethylbenzene over large pore size zeolites such as zeolite Y. Synthesis of zeolite ZSM-12 is described in U.S. Pat. No. 5,021,141 (Rubin), which is incorporated herein by reference. A process for ethylbenzene production over zeolite ZSM-12 is described in U.S. Pat. No. 5,907,073 (Kumar), which is incorporated herein by reference. Production of ethylbenzene over zeolite Mordenite is described in U.S. Pat. No. 5,430,211 (Pogue), which is incorporated herein by reference. Liquid phase synthesis of ethylbenzene with zeolite Beta is described in U.S. Pat. No. 4,891,458 (Innes) and U.S. Pat. No. 6,060,632 (Takamatsu), which are incorporated herein by reference. U.S. Pat. No. 4,849,569 (Smith), U.S. Pat. No. 4,950,834 (Arganbright), U.S. Pat. No. 5,086,193 (Sy), U.S. Pat. No. 5,113,031 (Sy), and U.S. Pat. No. 5,215,725 (Sy), which are incorporated herein by reference, teach various systems for the catalytic distillation production of alkylated aromatic compounds, including ethylbenzene and cumene.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom (e.g., N or S) are also useful provided they do not act as catalyst poisons under the reaction conditions selected. Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction. Suitable aromatic hydrocarbons include benzene, naphthalene, anthracene, naphthacene, perylene, coronene, and phenanthrene.

Generally the alkyl groups which can be present as substituents on the aromatic compound contain from 1 to about 22 carbon atoms and preferably from about 1 to 8 carbon atoms, and most preferably from about 1 to 4 carbon atoms. Suitable alkyl substituted aromatic compounds include toluene; xylene; isopropylbenzene; normal propylbenzene; alpha-methylnaphthalene; ethylbenzene; cumene; mesitylene; durene; p-cymene; butylbenzene; pseudocumene; o-diethylbenzene; m-diethylbenzene; p-diethylbenzene; isoamylbenzene; isohexylbenzene; pentaethylbenzene; pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. Reformate, especially reformate containing substantial quantities of benzene, toluene, and/or xylene, would also constitute a useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins can also be useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Typical aromatic alkylation reactions which may be improved by the present invention include obtaining ethylbenzene from the reaction of benzene with ethylene, cumene from the reaction of benzene with propylene, ethyltoluene from the reaction of toluene with ethylene, and cymenes from the reaction of toluene with propylene. The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C.; a pressure of from about 0.2 to about 250 atmospheres; and preferably from about 5 to about 100 atmospheres, a molar ratio of alkylatable aromatic compound to alkylating agent of from about 0.1:1 to about 50:1, and preferably can be from about 0.5:1 to about 10:1; and a feed weight hourly space velocity (WHSV) of between about 0.1 and 500 hr$^{-1}$, preferably between 0.5 and 100 hr$^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen. When benzene is alkylated with ethylene to produce ethylbenzene, the alkylation reaction may be carried out in the liquid phase. Suitable liquid phase conditions include a temperature between 150° C. and 316° C., preferably between 205° C. and 260° C.; a pressure up to about 3000 psig (20875 kPa); preferably between 400 and 800 psig (2860 and 5600 kPa), a space velocity between about 0.1 h$^{-1}$ and 20 h$^{-1}$ WHSV, preferably between 1 and 6 h$^{-1}$ WHSV, based on the ethylene feed; and a ratio of the benzene to the ethylene in the alkylation reactor from 1:1 to 30:1 molar, preferably from about 1:1 to 10:1 molar.

As regards the dry colorimetry analysis the principle has been explained above. A sample of the feedstock to be analyzed is vaporized, unless it is available under gasous phase, and is sent through a porous substrate carrying a reagent which changes color in proportion with the impurities. The liquid sample, if any, can be vaporized by any means. The porous substrate can be paper like filter paper. The porous substrate carries a chemical reagent specific to the nitrogen containing compounds impurities and advantageously responds to ammonia ($NH_3$ or $NH_4OH$), methylamine, dimethylamine, ethylamine and trimethylamine. This chemical reagent also reacts positively to $H_2S$ but normaly $H_2S$ is not present in the aromatic substrate feed and in the alkylating agent feed. The color is compared with standart colors obtained with samples containing known amounts of nitrogen containing compounds (the calibration). Any means can be used for the comparison. Advantageously an electronic device such as a photo optical system reads the color and by comparison with the standart colors converts the color to the amount of impurities. Advantageously the range is 30 wppb-25 wppm. The gas sample to be analyzed flows through the porous substrate carrying the reagent during about 1 to 5 minutes in accordance with the calibration.

To improve the response in time, many such apparatus can be used in parallel and a measurement is launched e.g. every minute or every ten seconds. Should the impurities are found to be higher than a requested level the reactor containing the catalyst can be temporarily by-passed. By way of example the above analysis can be made by an automatic device supplied by C.I. Analytics in Canada under the reference Sensi-tape® 7510.

During operation, the Sensi-Tape® is incremented through a sampling "window" where it is exposed to a metered sample stream. If the target gas is present, a stain proportional to the concentration develops. Simultaneously, a beam of light is reflected off the exposed portion of the tape and the intensity is measured continuously. As the amount of reflected light decreases due to stain development, the reduction is sensed by a photocell detector as an analog signal. This signal is converted to a digital format, matched to the gas response curve stored in the analyzer's permanent memory, and displayed/documented as the actual concentration value. All of these functions are microprocessor controlled. The use of this spectrophotometric technique, in combination with microprocessor control, provides excellent accuracy, repeatability, and detectability of low ppb (parts-per-billion) concentrations.

The invention claimed is:

1. A process for the alkylation of an aromatic substrate with an alkylating agent comprising:
   providing an alkylation reaction zone containing an alkylation catalyst;
   introducing a feedstock comprising an aromatic substrate, an alkylating agent, and an amount of nitrogen containing compounds selected from the group consisting of methylamine, dimethylamine, ethylamine, trimethylamine, and combinations thereof into an inlet of the alkylation reaction zone and into contact with the alkylation catalyst; wherein the aromatic substrate is benzene and the alkylating agent is ethylene;
   operating the alkylation reaction zone at temperature and pressure conditions sufficient to cause alkylation of the aromatic substrate with the alkylating agent in the presence of the alkylation catalyst to produce an alkylation product comprising a mixture of the aromatic substrate, monoalkylated aromatic components, and polyalkylated aromatic components;
   withdrawing the alkylation product from the alkylation reaction zone; wherein the amount of said nitrogen containing compounds in the feedstock are monitored in a range of from 15 to 35 wppm by dry colorimetry;
   wherein monitoring the amount of said nitrogen containing compounds comprises:
   vaporizing a sample of the feedstock, or obtaining a sample of the feedstock that is in the gaseous phase; and
   sending the sample through a porous substrate carrying a reagent that changes color in proportion with the amount of said nitrogen containing compounds.

2. The process of claim 1, wherein the alkylation reaction zone is operated in the liquid phase.

3. The process of claim 1, wherein the amount of said nitrogen containing compounds is monitored in a range of from 25 to 30 wppm.

4. The process of claim 1, wherein multiple dry colorimetry apparatus are used in parallel.

5. The process of claim 1, further comprising by-passing the alkylation reaction zone if the amounts of said nitrogen containing compounds is monitored to be higher than a requested level.

* * * * *